United States Statutory Invention Registration [19]

[11] Reg. Number: H951

Simpson [43] Published: Aug. 6, 1991

[54] PROCESS FOR CORN REGENERATION FROM TISSUE CULTURE

[75] Inventor: Sandra F. Simpson, Princeton Junction, N.J.

[73] Assignee: FMC Corporation, Philadelphia, Pa.

[21] Appl. No.: 207,100

[22] Filed: Jun. 15, 1988

[51] Int. Cl.[5] ..... A01H 4/00; A01H 5/00; C12N 5/04

[52] U.S. Cl. ..... 435/240.4; 435/240.48; 435/240.49; 435/240.5; 435/240.54; 800/200

*Primary Examiner*—Deborah L. Kyle
*Assistant Examiner*—Valerie Fee
*Attorney, Agent, or Firm*—Robert M. Kennedy; H. Robinson Ertelt; Robert L. Andersen

[57] ABSTRACT

The present invention relates to a process for corn regeneration from tissue culture which comprises the steps of (a) culturing corn tissue on a callus induction medium comprising the hormone picloram, mineral salts, vitamins, and sucrose to produce embryogenic callus;

(b) subculturing the embryogenic callus on a callus maintenance medium comprising the hormone picloram, mineral salts, vitamins, and sucrose for callus maintenance;

(c) subculturing the embryogenic callus on regeneration medium comprising mineral salts, vitamins, and sucrose to produce plantlets; and (d) subculturing the plantlets on maturation medium comprising mineral salts, vitamins, and sucrose for root and shoot development.

9 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR CORN REGENERATION FROM TISSUE CULTURE

This application pertains to the field of agricultural biotechnology, particularly as it related to the regeneration of corn plants by a process which, in part, utilizes corn tissue culture technology.

Processes for regenerating various genotypes of corn are known in the art. For example, U.S. Pat. No. 4,665,030 discloses a broadly applicable process for regenerating corn, including commercially important cultivars such as B73, A632, A619, CM105, B37, B84, B14, Mo17, and R168, which comprises the steps of (a) culturing tissue obtained from a corn plant on a first medium comprising mineral salts, vitamins, sucrose and a hormone selected from the group consisting of chloramben and dicamba for callus formation;

(b) subculturing said callus on a second medium comprising mineral salts, vitamins, sucrose and a hormone selected from the group consisting of chloramben, dicamba, a mixture of chloramben and ABA, and a mixture of dicamba and ABA for callus maintenance;

(c) subculturing said callus on a third medium comprising mineral salts, vitamins and sucrose for shoot and root formation; and (d) optionally subculturing said shoots and roots on a fourth medium comprising mineral salts, vitamins, and sucrose.

European Patent Application Publication No. 0,246,527, published Nov. 25, 1987, and a corresponding U.S. priority application, U.S. Ser. No. 865,431, filed May 21, 1986 disclose a process for regenerating corn plantlets from cell or tissue culture which comprises the steps of (a) culturing tissue obtained from a corn plant on a first medium comprising mineral salts, vitamins, sucrose and a hormone selected from the group consisting of (i) a hormone of formula I

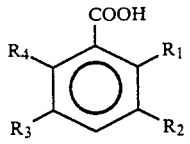

wherein $R_1$ and $R_3$ are identical and are selected from the group consisting of F, Cl, Br and I; $R_2$ is selected from the group consisting of $NH_2$, $NO_3$, OH, Cl and H; and $R_4$ is selected from the group consisting of Cl, $OCH_3$ and H and (ii) a mixture of a hormone of formula I and ABA for callus formation;

(b) subculturing said callus on a second medium comprising mineral salts, vitamins, sucrose and a hormone selected from the group consisting of (i) a hormone of formula I and (ii) a mixture of a hormone of formula I and ABA for callus maintenance; and (c) subculturing said callus on a third medium comprising mineral salts, vitamins, and sucrose to form shoots and roots, whereby plants are obtained.

Other prior art processes for regenerating corn from tissue culture are discussed in the U.S. patent and the EP publication discussed above. These other processes differ from the processes discussed above primarily in that a different hormone, e.g. 2,4-dichlorophenoxyacetic acid, is employed in the callus induction and maintenance media.

The critical step in the regeneration of corn, whatever cultivar, is, as taught in the U.S. patent and EP publication discussed above, the induction of callus formation. If callus can be induced from corn tissue, the references state, it can then be processed to regenerate plants. Once callus tissue has been formed, the regeneration process is applicable to all cultivars of corn.

It is well known in the art that a key to callus formation in plant systems in general and for the various cultivars of corn, is the inclusion in the callus induction medium of one or more hormones/auxins, such as those discussed above, at an appropriate concentration level.

It has now been discovered that the herbicide 4-amino-3,5,6-trichloropyridine-2-carboxylic acid, also known as picloram, is also an effective hormone for inducing callus formation and is broadly applicable, across cultivar lines, in corn tissue culture processes for corn regeneration. Examples of cultivars which may be regenerated by application of the present process include B73, A632, A619, CM105, B37, B84, B14, B14A, Mo17, R168, C103, CB59G, Oh43, A634, A188 x B37 hybrid, and W64A x B37 hybrid.

One aspect of the present invention pertains to the use of picloram in place of the hormones disclosed in the prior art process for corn regeneration from tissue culture. Picloram may be effectively substituted for the hormones employed in those processes in any or all of the process steps requiring the presence of a hormone, e.g. in the callus induction/formation step and/or the callus maintenance step of the processes of U.S. Pat. No. 4,665,030, EP Patent Application Publication No. 0,246,527, and U.S. patent application Ser. No. 865,341 (filed May 21, 1986) mentioned above.

The entire disclosures of U.S. Pat. No. 4,665,030, EP Patent Application Publication No. 0,246,527, and U.S. patent application Ser. No. 865,431 (filed May 21, 1986), as well as the pertinent disclosures of the references discussed or mentioned therein are incorporated herein by reference. Processes pertaining to corn regeneration from tissue culture disclosed in EP Patent Application Publication No. 256,165 (U.S. Priority application Ser. No. 897,422, filed Aug. 18, 1986), which discloses use of mature corn embryos as the explant source for callus induction and plant regeneration, and EP Patent Application Publication No. 256,166 (U.S. Priority application Ser. No. 897,209, filed Aug. 18, 1986), which discloses preconditioning the explant source for callus induction and plant regeneration, are applicable in the present process, and the disclosures in these EP publications and U.S. applications are also incorporated herein by reference.

Included within the scope of the present invention is a process for corn regeneration from tissue culture which comprises the steps of (a) culturing corn tissue on a callus induction medium comprising the hormone picloram, mineral salts, vitamins, and sucrose to produce embryogenic callus;

(b) subculturing the embryogenic callus on a callus maintenance medium comprising the hormone picloram, mineral salts, vitamins, and sucrose for callus maintenance or to produce plantlets;

(c) subculturing embryogenic callus and/or plantlets smaller than about 2 cm in height from step b) on regeneration medium comprising mineral salts, vitamins, and sucrose to produce plantlets, and (d) subculturing the plantlets from step (c) and/or plantlets greater than about 2 cm in height from step (b) on maturation medium comprising mineral salts, vitamins, and sucrose for root and shoot development.

In the present process the concentration of picloram in the culture medium for callus induction (e.g. step (a) in the process above) or callus maintenance (e.g. step (b) above) is in the range of 5 to 60 μM, preferably 10 to 40 μM. The composition of the callus induction medium qualitatively and quantitatively may be the same or different from the callus maintenance medium. Step (b) of the process may be repeated one or more times if desired. The corn tissue in step (a) is mature or, preferably, immature embryos.

A characteristic of the present process is the production of embryogenic callus, which may be accompanied by nonembryogenic callus, in the callus induction step. The embryogenic callus, preferably uncontaminated with nonembryogenic callus, is the callus selected for subculture in step (b). Embryogenic callus may be distinguished from nonemryogenic callus as described by Duncan et al., Planta, 165, 322–332 (1985), incorporated herein by reference. The embryogenic callus is hard, irregularly shaped, nodular, and white or yellow in color, whereas nonembryogenic callus is soft, granular appearing, and gray-yellow in color.

As described in Example 3 below, a few plantlets may be formed during step (b). Plantlets attaining a height of at least about 2 cm during step (b) may be subcultured directly in maturation medium (step (d)) for root and shoot development. Otherwise, plantlets (those smaller than about 2 cm) and calli from step (b) are subcultured (preferably separately) on regeneration medium in step (c).

The present invention is further illustrated by the following examples.

EXAMPLE 1

Preparation of Solutions

The following stock solutions were prepared for use in making the media described in further detail below. Double distilled, deionized water was used in the preparation of each stock solution. After preparation each stock solution was refrigerated.

1. Ammonium Sulfate/Potassium Nitrate

A one liter stock solution was prepared by dissolving 23.15 grams of ammonium sulfate and 141.5 grams of potassium nitrate in 500 ml of water. This solution was diluted to one liter with water.

2. Calcium Chloride

A one liter stock solution was prepared by dissolving 44.0 grams of calcium chloride dihydrate in 500 ml of water. This solution was diluted to one liter with water.

3. Potassium Dihydrogen Phosphate / Magnesium Sulfate Heptahydrate

A one liter stock solution was prepared by dissolving 40.0 grams of potassium dihydrogen phosphate and 18.5 grams of magnesium sulfate heptahydrate in 500 ml of water. The solution was diluted with water to one liter.

4. Micronutrients

The micronutrient stock solution was prepared according to the method described by Gamborg et al., Plant Tissue Culture Methods and Applications in Agriculture, Edited by T. A. Thorpe, Academic Press, 1981, pp 21–44, incorporated herein by reference, for the 'B5 Micronutrient Stock'. One liter of this solution was prepared.

5. Ethylenediaminetetraacetic Acid, Disodium Salt / Iron (II) Sulfate Heptahydrate A one liter stock solution was prepared by dissolving 3.724 grams of ethylenediaminetetraacetic acid, disodium salt and 2.784 grams of iron (II) sulfate heptahydrate in 500 ml of water. This solution was diluted with water to a volume of one liter.

6. L-Proline (lM)

The L-proline stock solution was prepared by dissolving 115.1 grams of L-proline in 500 ml of water. This solution was diluted with water to a volume of one liter.

7. Thiamine Hydrochloride

A 100 ml stock solution was prepared by dissolving 100 mg of thiamine hydrochloride in 50 ml of water. This solution was diluted to 100 ml with water.

8 RT Vitamin Solution

One liter of RI vitamin solution was prepared according to the method of Horn et al., Plant Physiol., 72, 426–429 (1983), incorporated herein by reference.

9. Picloram Solution

A $1\times10^{-3}$M solution of 4-amino-3,5,6-trichloropicolinic acid (picloram) was prepared by dissolving 0.024 gram of picloram in 5 ml of acetone. Water was added to a volume of 100 ml.

EXAMPLE 2

Preparation of Media

1. Medium One—Callus Induction / Maintenance Medium

The first medium was prepared by adding the following amounts of stock solutions 1–9 to 500 ml of stirred double distilled deionized water:

| Stock Solution | ml |
|---|---|
| 1 | 20.0 |
| 2 | 3.77 |
| 3 | 10.0 |
| 4 | 10.0 |
| 5 | 10.0 |
| 6 | 12.0 |
| 7 | 0.371 |
| 8 | 1.0 |
| 9 | 10.0 |

To the resultant solution was added 0.50 gram of Bacto Vitamin Assay Casamino Acids, Dehydrated (Difco Laboratories) and 19.5 grams of sucrose. The pH of this solution was adjusted to 5.8 (using dilute aqueous potassium hydroxide solution). This solution was diluted with double distilled, deionized water to a volume of 900 ml and 8.0 grams of agar (Difco Laboratories) was added. The resultant solution was sterilized in an autoclave, 225° C. and 15 psi, for twenty-five minutes. A glucose solution was prepared by dissolving 10.0 grams of glucose in 95 ml of double distilled, deionized water. This glucose solution was filter sterilized through a 0.2 L- micron Millipore® filter and added aseptically to the cooling, autoclaved medium. After thorough mixing, the medium was poured into petri dishes. The concentration of picloram in each petri dish was 10 μM.

2. Medium Two—Regeneration Medium

The regeneration medium was prepared in the same manner as the first medium except Stock Solution 9 was not included (10 ml of double distilled, deionized water was used in place of Stock Solution 9).

3. Medium Three—Maturation Medium

The maturation medium was prepared in a manner similar to that described by Murashige and Skoog, Physiol. Plant., 15, 473–497 (1962), incorporated herein by reference, with the following modifications:

a) The present medium was one-third strength with respect to the ingredients other than sucrose, auxin/-hormone, and agar, i.e. ingredient concentrations other than the noted exceptions were one-third the reported concentrations;
b) Ten grams/L rather than 20 grams/L of sucrose was used;
c) No auxin / hormone was used; and
d) Seven grams/L rather than 10 grams/L of agar was used.

This medium was dispensed into culture tubes or Magenta GA7 ® vessels. The filled culture tubes or GA7 vessels were sterilized in an autoclave for 20–25 minutes.

EXAMPLE 3

Corn Regeneration

Immature embryos were isolated from the cob of the corn (*Zea mays* L.) cultivar A188 ten to fourteen days post pollination when the embryos were 1.5–2.0 mm in length. The cob was harvested and surface sterilized in a solution containing 30% Clorox ® bleach (1.6% sodium hypochlorite) and 1–2 drops of Tween-20 ® surfactant for 20 minutes. The cobs were rinsed three times with double distilled, deionized water. The immature embryos were isolated by slicing off the top of each kernel with a scalpel and scooping out the endosperm. The immature embryos were removed with a spatula and plated onto medium one, ten emboryos per petri dish, so that the embryo axis was in contact with the medium, i.e., the scutellar side was up. The first medium, the callus induction-maintenance medium, was prepared as described in Example 1. The petri dishes, five dishes with a total of 46 embryos, were cultured for three weeks under the following conditions:

Temperature 28° C. (constant)
Photoperiod 16 hr:8 hr (light:dark)
Light sources Gro-Lux 20w and Cool White 40w
Light intensity at petri plate approximately 100 μ Einstein/$m^2$/sec.

At the end of three weeks, the first subculture point, the calli in each petri dish were visually assessed as to embryogenic potential as described above and by Duncan et al., planta, 165, 322–332 (1985). At this time, embryogenic calli were excised from the immature embryo, and any roots which had formed were removed from each callus. The excised calli were placed on fresh medium one, ten calli per plate. These plates were cultured for three weeks under the same conditions described above. At the end of the three weeks, the second subculture point, each callus was visually assessed as to embryogenic potential as described above. It was determined that 27 (59%) of the calli appeared capable of regeneration. This represents 59% embryogenic potential.

In some cases, plantlets regenerated from the calli on the second culture. Those plantlets which were greater than 2 cm in height were excised and were placed into culture tubes containing medium three, one plantlet per tube. Those plantlets which were less than 2 cm in height were excised and placed in petri dishes containing medium two. The plantlets on medium two were cultured for three to six weeks. When a height of at least 2 cm was attained, the plantlets were placed into culture tubes containing medium three, one plantlet per tube.

The remaining calli were replated to petri dishes containing medium two. These plates were cultured for three to six weeks under the previously described conditions. Plantlets which regenerated, and were of sufficient size, were excised from the calli and were placed culture tubes containing medium three, one plantlet per tube.

The plantlets in culture tubes containing medium three were cultured for one to five weeks under the previously described conditions. Those plantlets which had formed roots were removed from the culture tubes, and the roots were carefully rinsed with distilled water to remove the agar medium. The rooted plantlets were planted in two inch planting pots containing sterilized vermiculite, one plant per pot. These pots were placed in a high humidity chamber and kept moist for seven to ten days at which time the lid was lifted for five to seven days for slow acclimation to lower humidity.

When roots were visible through the bottom of the two inch pots, the plants were transplanted into six inch pots containing a 50:50 mixture of vermiculite and Promix ® potting soil. These plants were kept in an environmental growth chamber or a greenhouse and were watered once daily and fertilized twice a week. The plants were transplanted into larger pots as needed.

EXAMPLE 4

Callus Induction

Immature embryos were isolated from the following cultivars of corn and were plated onto medium one as described in Example 3: *Zea mavs* L. cultivar B73, C103, hybrid A188×B37, and hybrid W64A×B37. Calli were obtained and had similar or better general appearance than the calli of Example 3. At the second subculture point on medium one, the calli were ready for transfer to medium two. The following table presents the percent embryogenic potential (%E-Pot) determined at the second subculture point.

| Cultivar | No. of Embryos Plated | % E-Pot |
|---|---|---|
| B73 | 82 | 30 |
| C103 | 86 | 25 |
| hybrid A181xB37 | 30 | 16 |
| hybrid W64AxB37 | 14 | 81 |

EXAMPLE 5

Callus Induction

Immature embryos were isolated from the following cultivars of corn and were plated onto medium one as described in Example 3: *Zea mays* L. A632, B14A, B37, CB59G, Mo17, and Oh43. Calli were obtained and had a general appearance which was not as good as the calli of Example 3. At the second subculture point: on medium one, the calli were ready for transfer to medium two. The following table presents the percent embryogenic potential (%E-Pot) determined at the second subculture point.

| Cultivar | No. of Embryos Plated | % E-Pot |
|---|---|---|
| A632 | 144 | 3 |
| B14A | 180 | <1 |
| B37 | 369 | 3 |
| CB59G | 177 | <1 |
| Mo17 | 130 | 5 |
| Oh43 | 39 | 5 |

EXAMPLE 6

Regeneration of Corn Cultivars Using Varying Rates of Picloram

One liter of Duncans "D" medium was prepared as described by Duncan et al., Planta, 165, 322–332 (1985), incorporated herein by reference. The medium was poured into 20 petri dishes providing approximately 50 ml of media per plate.

A $5\times10^{-2}$M stock solution of picloram was prepared by dissolving 24.2 mg of picloram in 2.0 ml of acetone. Aseptic conditions were maintained throughout the following portions of this experiment. Ten microliters of the picloram stock solution was placed on a 0.5 inch filter paper disk, and the disk was allowed to air dry. The dried disk was placed in the center of a petri dish containing 50 ml of Duncans "D" medium. The treated petri plate was allowed to equilibrate for 24 hours at room temperature, resulting in a 10 μM concentration of picloram in the medium. This process was repeated using 20, 30, and 40 microliters of the picloram stock solution per 0.5 inch disks, resulting in 20 μM, 30 μM, and 40 μM concentrations of picloram, respectively, in the media of each plate.

Immature embryos were isolated from the following cultivars and plated, usually eight per plate, on the picloram-treated media described above using the procedure described in Example 3 *Zea mays* L. W64A, B37, B73, and A188. The following table summarizes the results of callus embryogenic potential determined at the second subculture point.

| Cultivar | Conc. (μM) of Picloram | Total Calli | Total E-Calli[a] |
|---|---|---|---|
| W64A | 10 | 12 | 1 |
| | 20 | 49 | 2 |
| | 30 | 28 | 2 |
| | 40 | 18 | 4 |
| B37 | 10 | 20 | 8 |
| | 20 | 25 | 17 |
| | 30 | 28 | 18 |
| | 40 | 34 | 19 |
| B73 | 10 | 44 | 7 |
| | 20 | 76 | 40 |
| | 30 | 54 | 28 |

-continued

| Cultivar | Conc. (μM) of Picloram | Total Calli | Total E-Calli[a] |
|---|---|---|---|
| | 40 | 59 | 33 |
| A188 | 10 | 0 | — |
| | 20 | 9 | 6 |
| | 30 | 7 | 3 |
| | 40 | 8 | 3 |

[a]number of calli which, upon visual inspection, appeared capable of regeneration.

The calli were subcultured on the picloram-treated media on or more times, then were transferred to medium two, regeneration medium.

One of the cultivars, B73, was successively transferred to medium two and medium three, and regenerated plantlets. Some of these plantlets were transferred into two inch pots as described in Example 3.

I claim:

1. A process for corn regeneration from tissue culture which comprises the steps of (a) culturing corn tissue on a callus induction medium comprising the hormone picloram, mineral salts, vitamins, and sucrose to produce embryogenic callus;

(b) subculturing the embryogenic callus on a callus maintenance medium comprising the hormone picloram, mineral salts, vitamins, and sucrose for callus maintenance or two produce plantlets;

(c) subculturing embryogenic callus and/or plantlets smaller than about 2 cm in height from step (b) on regeneration medium comprising mineral salts, vitamins, and sucrose to produce plantlets, and (d) subculturing the plantlets from step (c) and/or plantlets greater than about 2 cm in height from step (b) on maturation medium comprising mineral salts, vitamins, and sucrose for root and shoot development.

2. The process of claim 1 in which the concentration of picloram in the media in steps (a) and (b) is in the range of 5 to 60 μM.

3. The process of claim 2 in which the concentration of picloram in the medium in step (a) is the same as in step (b) and is in the range of 10 to 40 μM.

4. The process of claim 1 in which the tissue is from immature or mature embryos.

5. The process of claim 4 in which the tissue is from immature embryos.

6. The process of claim 5 in which the concentration of picloram in the media in steps (a) and (b) and is in the range of 5 to 60 μM.

7. The process of claim 6 in which the concentration of picloram in the medium in step (a) is the same as in step (b) and is in the range of 10 to 40 μM.

8. In a process for corn regeneration from tissue culture which comprises a step of embryogenic callus induction on a medium comprising a hormone and a subsequent step of subculturing embryogenic callus on a medium comprising a hormone for callus maintenance or plantlet formation, the improvement therein which comprises employing picloram, at a concentration in the range of 5 to 60 μM, as the hormone in the earlier step or in the subsequent step or in both steps.

9. The process of claim 8 in which picloram is the hormone in both steps.

* * * * *